United States Patent [19]

Naito et al.

[11] 4,138,554

[45] Feb. 6, 1979

[54] 7-[D-α-(4-HYDROXY-1,5-NAPHTHYRIDINE-3-CARBOXAMIDO)-α-PHENYL (AND P-HYDROXYPHENYL)ACETAMIDO]-3-CARBAMOYLOXYMETHYL-3-CEPHEM-4-CARBOXYLIC ACIDS

[75] Inventors: Takayuki Naito, Kawasaki; Jun Okumura; Masahisa Oka, both of Yokohama, all of Japan

[73] Assignee: Bristol-Myers Company, New York, N.Y.

[21] Appl. No.: 804,963

[22] Filed: Jun. 9, 1977

Related U.S. Application Data

[63] Continuation-in-part of Ser. No. 784,870, Apr. 5, 1977, abandoned.

[51] Int. Cl.$^2$ ............................................. C07D 501/34
[52] U.S. Cl. ........................................ 544/22; 544/30; 424/246
[58] Field of Search ................................... 544/22, 28

[56] References Cited

U.S. PATENT DOCUMENTS 4,041,161   8/1977   Kocsis et al. ..................... 544/22

FOREIGN PATENT DOCUMENTS 2520561  11/1975  Fed. Rep. of Germany ............. 544/22
2614303  10/1976  Fed. Rep. of Germany ............. 544/30

OTHER PUBLICATIONS

Flynn "Cephalosporins and Penicillins" 1972, pp. 544 and 556.

Primary Examiner—Raymond V. Rush
Assistant Examiner—David E. Wheeler
Attorney, Agent, or Firm—Herbert W. Taylor, Jr.

[57] ABSTRACT

7-[D-α-(4-hydroxy-1,5-naphthyridine-3-carboxyamido)-α-phenyl (and p-hydroxyphenyl) acetamido]-3-carbamoyloxymethyl-3-cephem-4-carboxylic acids were synthesized and found to have potent antibacterial activity in vitro especially against many strains of *Pseudomonas aeruginosa*.

45 Claims, No Drawings

7-[D-α-(4-HYDROXY-1,5-NAPHTHYRIDINE-3-CARBOXAMIDO)-α-PHENYL (AND P-HYDROXYPHENYL)ACETAMIDO]-3-CARBAMOYLOXYMETHYL-3-CEPHEM-4-CARBOXYLIC ACIDS

CROSS-REFERENCE TO RELATED APPLICATION

This application is a continuation-in-part of our prior, copending application Ser. No. 784,870 filed Apr. 5, 1977 now abandoned.

BACKGROUND OF THE INVENTION

1. Field of the Invention

The compounds of the present invention belong to the class of antibacterial agents commonly called cephalosporins.

2. Description of the Prior Art

Sumitomo's West Germany Offenlegungsschrift No. 2,614,303 laid open Oct. 14, 1976 (and Japan Kokai No. 51-115491) describes cephalosporins having the general formula

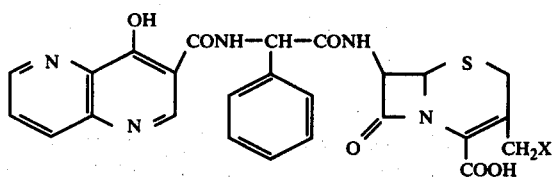

in which X is exemplified as acetoxy or a heterocyclic mercapto group such as 2-methyl-1,3,4-thiadiazol-5-yl, 1-methyl-tetrazol-5-yl and 1,2,3-triazol-5-yl.

Cephalosporins included under the general formula

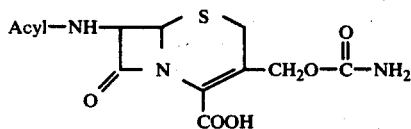

are described, for example, in U.S. Pat. No. 3,905,963 in which Examples II and VII are titled "Preparation of 7-[D(-)-α-aminophenylacetamido]-3-carbamoyloxymethyl-3-cephem-4-carboxylic Acid" and "Preparation of Benzhydryl 7-[D(-)-α-(t-butoxycarbamido)-phenylacetamido]-3-carbamoyloxymethyl-3-cephem-4-carboxylate", respectively and Claim 1 reads A process for preparing a compound having the formula

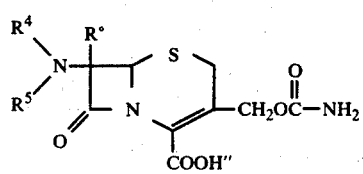

which comprises the sequence of reacting a compound of the formula

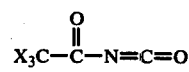

with an N-substituted isocyanate of the formula

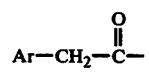

in which X is halogen, to produce a corresponding 3-(N-substituted) carbamoyloxymethyl derivative, and cleaving the N-substituent in the presence of silica gel, an aqueous buffer solution having a pH of from about 5 to about 9, an alkali or alkaline earth metal carbonate, bicarbonate, or sulfite, or zinc with a $C_1$-$C_4$ alcohol or an acid having a pK value greater than about 3 to produce the desired 3-carbamoyloxymethyl cephalosporin derivative, in which, in the foregoing formulae, R° is hydrogen or methoxy, $R_4$ is hydrogen and $R_5$ is $C_1$-$C_8$ alkanoyl; azidoacetyl; cyanoacetyl; haloacetyl;

in which Ar is phenyl, thienyl, furyl, pyrrolyl, or phenyl substituted with from one to three substituents selected from the group consisting of fluorine, chlorine, bromine iodine, trifluoromethyl, hydroxy, $C_1$-$C_3$ alkyl, $C_1$-$C_3$ alkoxy, cyano, and nitro;

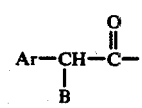

in which Ar' is phenyl, pyridyl, or substituted phenyl as defined above, and Y is oxygen or sulfur;

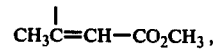

in which Ar is as defined above, and B is a hydroxyl or carboxyl group protected by esterification; —CH; —$N_3$; or —NHR in which R is benzyloxycarbonyl, $C_1$-$C_4$ alkoxycarbonyl, cycloalkoxycarbonyl, triphenylmethyl, $$CH_3\overset{|}{C}=CH-CO_2CH_3,$$

or 2,2,2-trichloroethoxycarbonyl; (3-sydnone)$C_2$-$C_3$ alkanoyl;

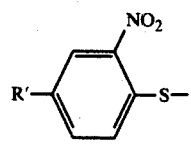

in which R' is hydrogen or methoxy; 2-(1H-tetrazol-1-yl)acetyl;

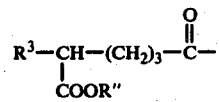

in which R" is as herein defined, and R³ is amino or an acylamido group in which the acyl group is $C_1$-$C_4$ alkanoyl, $C_6$-$C_{12}$ aroyl, $C_1$-$C_4$ alkoxycarbonyl, benzyloxycarbonyl, $C_5$-$C_6$ cycloalkoxycarbonyl, $C_6$-$C_{12}$ aryloxycarbonyl, phthaloyl, or one of the above groups substituted with from one to three groups each selected from the group consisting of $C_1$-$C_4$ alkyl, halo, nitro, $C_1$-$C_4$ alkoxy, cyano; or $R^4$ and $R^5$ taken together with the nitrogen to which they are bonded is phthalimido or a cyclic imide moiety of a $C_3$-$C_{12}$ dicarboxylic acid, and R" is hydrogen, an amine salt cation of dicyclohexylamine, triethylamine, or tributylamine, or a carboxy protecting group selected from the group consisting of $C_1$-$C_6$ alkyl, 2,2,2-trihaloethyl, 2-iodoethyl, $C_5$-$C_7$ tert-alkenyl, $C_5$-$C_7$ tert-alkynyl, benzyl, nitrobenzyl, tetrahydropyranyl, succinimidomethyl, phthalimidomethyl, methoxybenzyl, dimethoxybenzyl, cyanomethyl, nitrophenyl, dinitrophenyl, 2,4,5-trinitrophenyl, bis(p-methoxyphenyl)methyl, triphenylmethyl, benzhydryl, benzyloxymethyl, $C_2$-$C_6$ alkanoyloxymethyl, $C_2$-$C_4$ alkanoyl, phenacyl, and a radical of the formula $$R^2_{\phantom{2}}\!\!-\!\!\underset{\underset{R^2}{|}}{\overset{\overset{R^2}{|}}{Si}}\!\!-$$

in which each $R^2$ independently is $C_1$-$C_4$ alkyl or halo selected from the group consisting of bromo, chloro, fluoro, and iodo, subject to the limitation that at least one $R^2$ is $C_1$-$C_4$ alkyl.

Intermediates such as diphenylmethyl 7β-amino-3-trichloroacetylcarbamoyloxymethylceph-3-em-4-carboxylate and diphenylmethyl-7β-amino-3-carbamoyloxymethylceph-3-em-4-carboxylate and its toluene-p-sulfonic acid salt are among the compounds described in U.S. Pat. No. 3,966,717. Desacetylcephaloglycine is described in U.S. Pat. No. 3,560,489.

As additional examples, Derwent's Farmdoc abstract 38079X discloses compounds of the formula

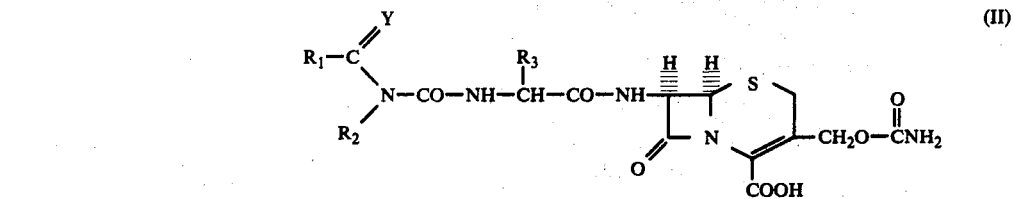

where Y=O or S; $R_1$= 1-20C organic radical; $R_2$= 1-3C alkyl or benzyl; $R_1$ + $R_2$ completes a 5, 6 or 7 membered ring opt. containing other hetero atoms; $R_3$ = phenyl (opt. substd. by one or more hydroxy, halo, nitro, 1-3C alkoxy or amino), 2- or 3-thienyl, 3-7C cycloalkyl or 1-4C alkyl, and Farmdoc 59670X discloses compounds of the formula

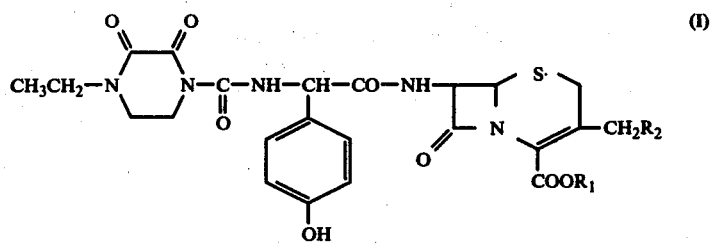

where $R_1$ = H, a cation or a blocking group and $R_2$ = acetoxy, carbamyloxy, 5-methyl-1,3,4-thiadiazol-2-ylthio or 1-methyl-1,2,3,4-tetrazol-5-ylthio.

U.S. Pat. No. 3,945,995 describes the preparation of the N-hydroxysuccinimido ester of 4-hydroxy-1,5-naphthyridine-3-carboxylic acid.

Compounds included under the general formula

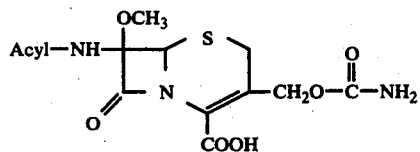

are called cephamycins rather than cephalosporins. Well-known examples are cefoxitin and cephamycin C in which acyl represents

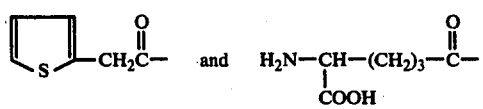

respectively (see the Merck Index, Ninth Edition, Monograph numbers 1912 and 1940). For examples, see U.S. Pat. Nos. 3,775,410; 3,780,034; 3,780,037; and 3,887,549 (in which acyl includes 2-phenylglycyl and the like). For the latter compound (both with and without the 7-methoxy substituent) see also R. Nagarajan et al., J. Amer. Chem. Soc. 93, 2308–2310 (1971).

SUMMARY OF THE INVENTION

There is provided by the present invention the acids having the D-configuration in the 7-sidechain and the formula

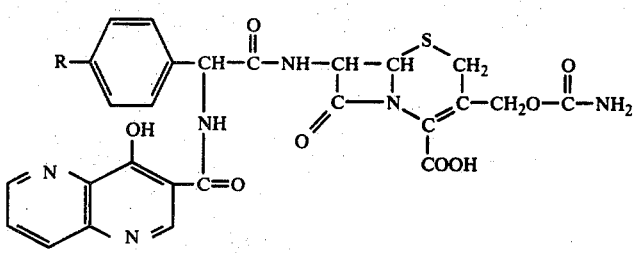

wherein R is hydrogen or hydroxy.

Also included within the present invention are pharmaceutically acceptable salts of those acids and also easily hydrolyzed esters of those acids including especially the pivaloyloxymethyl, acetoxymethyl, methoxymethyl, acetonyl, phenacyl, silyl such as trimethylsilyl, 3-phthalidyl, 5-indanyl, p-nitrobenzyl and β,β,β-trichloroethyl esters.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-β-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin.

There is also provided, according to the present invention, the process for the preparation of a compound having the formula

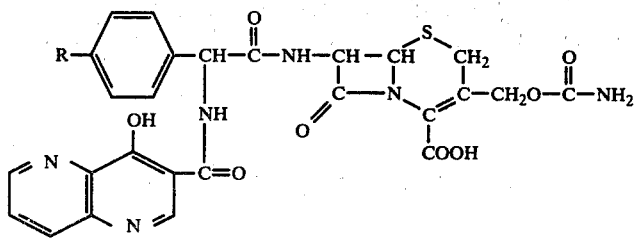

wherein R is hydrogen or hydroxy and the nontoxic salts and easily hydrolyzed esters thereof which comprises reacting a compound of the formula

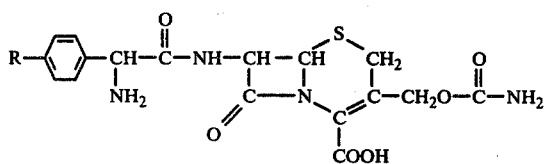

wherein R is hydrogen or hydroxy or a salt or easily hydrolyzed ester or Schiff base (as with benzaldehyde) thereof with an acylating derivative of the acid having the formula

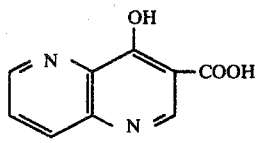

The compounds of the present invention are prepared according to the present invention by coupling with the compound designated II, that is, 7-D-α-amino-α-phenyl (or p-hydroxyphenyl) acetamido-3-carbamoyloxymethyl-3-cephem-4-carboxylic acid or a salt or easily hydrolyzed ester or Schiff base as with benzaldehyde thereof (including but not limited to those of U.S. Pat. No. 3,284,451 and U.K. Pat. No. 1,220,453 and any of the silyl esters described in U.S. Pat. No. 3,249,622 for use with 7-aminopenicillanic acid and used in Great Britain Pat. No. 1,073,530 and particularly the pivaloyloxymethyl, acetoxymethyl, methoxymethyl, acetonyl, phenacyl, p-nitrobenzyl and β,β,β-trichloroethyl esters) the acid III or its functional equivalent as an acylating agent for a primary amino group.

Thus, with respect to said acid III to be used to couple with compound II, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g., with p-nitrophenyl, 2,4-dinitrophenol, thiophenol, thioacetic acid) may be used or the free acid itself may be coupled with compound II after first reacting said free acid with N,N'-dimethylchloroforminium chloride [cf. Great Britain Pat. No. 1,008,170 and Novak and Weichet, Experientia XXI, 6, 360 (1965)] or by the use of enzymes or of an N,N'-carbonyldiimidazole or an N,N'-carbonylditriazole (cf. South African patent specification No. 63/2684) or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew. Chem. International Edition 3, 582, (1964)] or of an isoxazolium salt reagent [cf. R. B. Woodward, R. A. Olofson and H. Mayer, J. Amer. Chem. Soc. 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat.

No. 3,651,050) or of diphenylphosphoryl azide [DPPA; J. Amer. Chem. Soc., 94, 6203–6205 (1972) ] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring obtaining at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the acid III as described above with compound II (or a salt or preferably an easily hydrolyzed ester or Schiff base, as with benzaldehyde, thereof) it is also convenient and efficient to utilize as the coupling agent N-ethoxycarbonyl-2-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excipients. The dosage units are preferably in the form of liquid preparations such as solutions or suspensions. HP-20 is a macroreticular adsorbent resin in the form of insoluble beads of porous polymer. They are macroporous-nonionic, cross-linked polystyrene polymers.

DESCRIPTION OF THE PREFERRED EMBODIMENTS

EXAMPLE 1

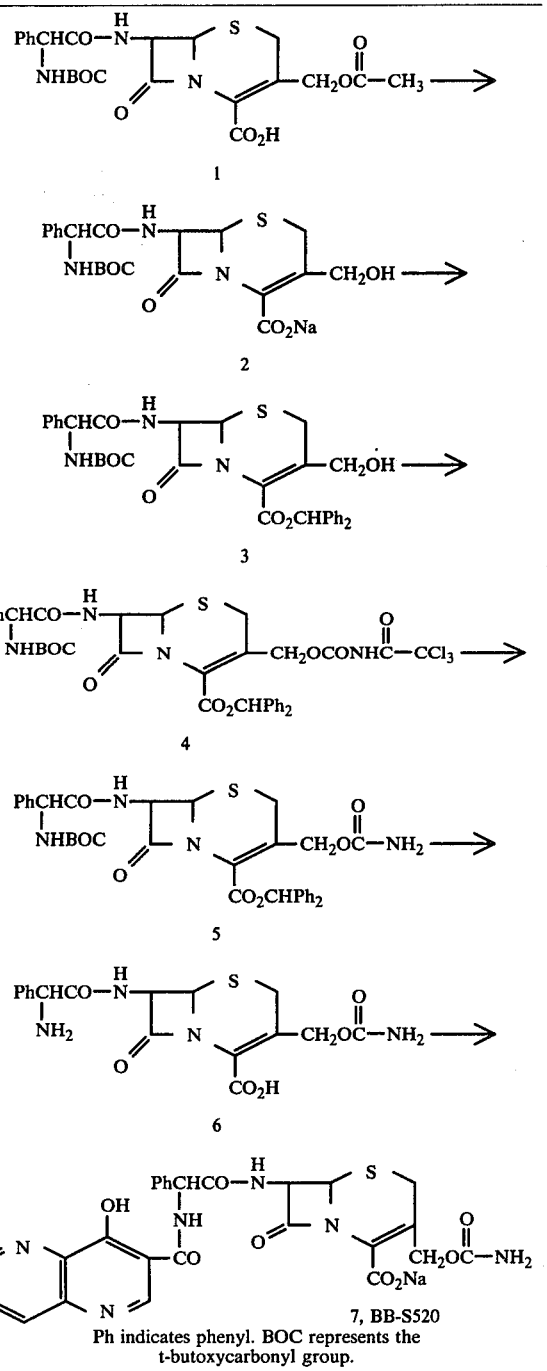

Ph indicates phenyl. BOC represents the t-butoxycarbonyl group.

Experimental Sodium 7-(D-α-t-butoxycarbonylamino-α-phenylacetamido)-cephalosporadesate (2)

To a suspension of 7-(D-α-t-butoxycarbonylamino-α-phenylacetamido)cephalosporanic acid (1, 951 mg., 2 m. moles) in 8 ml. of water was added 4 ml. of N NaOH at 7° C. in one portion with stirring. The reaction mixture was kept for 30 minutes under ice-cooling and then chromatographed on a column of a macroreticular non-ionic adsorbent resin (HP-20 DIAION, NIPPON RENSUI CO., 70 ml). The column was developed successively with water (220 ml.), 10% aq. MeOH (methanol) (220 ml.), 50% aq. MeOH (150 ml). and MeOH. The eluate was collected in 20-ml. fractions monitoring with uv (260 nm). The fractions 19–30 were combined and evaporated to a small volume under reduced pressure and lyophilized to afford 510 mg. (53%) of 2 melting at 181°–185° C. (dec.).

ir: $\nu_{max}^{KBr}$ 3400, 1765, 1690, 1680, 1600 cm$^{-1}$.

uv: $\lambda_{max}^{H_2O}$ 260 nm ($\epsilon$ 6400).

nmr: $\delta_{ppm}^{D_2O}$ 1.40 (9H, s, t-Bu-H), 3.16 & 3.53 (each 1H, d, J=18 Hz, 2-H), 4.19 (2H, s, 3-C$\underline{H}_2$), 4.94 (1H, d, J=4.5 Hz, 6-H), 5.17 (1H, s, C$\underline{H}$CO), 5.58 (1H, d, J=4.5 Hz, 7-H), 7.39 (5H, s, Ph-H).

Anal. Calculated for $C_{21}H_{24}N_3O_7SNa\cdot2H_2O$: C, 48.36; H, 5.41; N, 8.06; S, 6.15. Found: C, 48.59; H, 4.61; N, 7.76; S, 6.41.

Benzhydryl 7-(D-α-t-butoxycarbonylamino-α-phenylacetamido)-cephalosporadesate (3)

A solution of 2 (455 mg., 1 m.mole) in 3 ml. of water was layered with AcOEt (ethyl acetate) (10 ml.), cooled to 0° C. and adjusted to pH 3 with 10% HCl under stirring. The AcOEt layer was separated and the aqueous layer was extracted with AcOEt (2 × 10 ml.). The extracts were combined, washed with saturated aqueous NaCl (2 × 5 ml.) and dried over MgSO$_4$. To the extracts was added a solution of diphenyldiazomethane (about 5 m.moles) in AcOEt (20 ml.) at 5°–10° C. with stirring. The reaction mixture was stirred overnight at room temperature and evaporated to dryness under reduced pressure. The residue was washed with n-hexane (4 × 15 ml.), dissolved in THF (tetrahydrofuran) (5 ml.) and filtered to remove insolubles. The filtrate was diluted with n-hexane and the resulting precipitate was collected by filtration to afford 530 mg. (92%) of 3, melting at 115°–118° C.

ir: $\nu_{max}^{KBr}$ 3300, 1790, 1720, 1690 cm$^{-1}$.

uv: $\lambda_{max}^{EtOH}$ 260 nm ($\epsilon$ 5200).

nmr: $\delta_{ppm}^{DMSO-d_6}$ 1.36 (9H, s, t-Bu-H), 3.45 (2H, br-s, 2-H), 4.12 (2H, s, 3-C$\underline{H}_2$), 4.96 (1H, d, J=4.5 Hz, 6-H), 5.29 (1H, d, J=9 Hz, a singlet by addition of D$_2$O, C$\underline{H}$CO), 5.67 (1H, d-d, J=4.5, 7.5 Hz, a doublet J=4.5 Hz by addition of D$_2$O, 7-H), 6.79 (1H, s, C$\underline{H}$Ph$_2$), 7.24 (15H, m, Ph-H), 9.10 (1H, d, J=7.5 Hz, disappeared by addition of D$_2$O, 7-NH).

Anal Calculated for $C_{34}H_{35}N_3O_7S$: C, 64.85; H, 5.60; N, 6.67; S, 5.09. Found: C, 64.84; H, 5.65; N, 6.18; S, 4.96.

Benzhydryl 7-(D-α-butoxycarbonylamino-α-phenylacetamido)-3-trichloroacetylcarbamoyloxymethyl-3-cephem-4-carboxylate (4)

Trichloroacetylisocyanate (2.5 g., 13 m.moles) was added to a solution of 3 (4.1 g., 6.5 m.mol.) in dry acetone (12 ml.) at −5 to 0° C. with stirring. The reaction mixture was stirred at room temperature for 1.5 hr. The colorless crystals were collected by filtration, washed with acetone (5 ml.) and dried to afford 3.2 g. (60%) of 4, melting at 209–210° C.

ir: $\nu_{max}^{KBr}$ 3350, 1790, 1780, 1710, 1660, 1630 cm$^{-1}$.

uv: $\lambda_{max}^{EtOH}$ 257 nm ($\epsilon$ 9500).

nmr: $\delta_{ppm}^{DMSO-d_6}$ 1.39 (9H, s, t-Bu-H), 3.55 (2H, br-S, 2-H), 4.83 (2H, s, 3-C$\underline{H}_2$), 5.01 (1H, d, J=4.5 Hz, 6-H), 5.30 (1H, d, J=9 Hz, a singlet by addition of D$_2$O C$\underline{H}$CO), 5.75 (1H, d-d, J=4.5 & 7.5 Hz, a doublet J=4.5 Hz by addition of D$_2$O 7-H), 6.84 (1H, s, C$\underline{H}$Ph$_2$), 7.25 (15H, s, Ph-H), 9.10 (1H, d, J=7.5, disappeared by addition of D$_2$O, 7-N$\underline{H}$).

Benzhydryl 7-(D-α-t-butoxycarbonylamino-α-phenylacetamido)-3-carbamoyloxymethyl-3-cephem-4-carboxylate (5)

A mixture of 4 (1.5 g., 1.8 m.moles) and Na$_2$CO$_3$ (150 mg.) in 3 ml. of water and 14 ml. of THF was stirred at room temperature for 3 hours. The reaction mixture was evaporated and the aqueous residue was extracted with AcOEt (2 × 15 ml.). The combined AcOEt extracts were washed with saturated aqueous NaCl, dried over MgSO$_4$ and evaporated under reduced pressure. The residue (1.5 g.) was chromatographed on a silica-gel column eluting with 3% CHCl$_3$-MeOH to afford 490 mg. (40%) of 5 melting at 176–178° C.

ir: $\nu_{max}^{KBr}$ 3350, 1790, 1710, 1640 cm$^{-1}$.

uv: $\lambda_{max}^{EtOH}$ 259 nm ($\epsilon$ 7500).

nmr: $\delta_{ppm}^{DMSO-d_6}$ 1.37 (9H, s, t-Bu-H), 3.47 (2H, br-s, 2-H), 4.58 (2H, m, 3-C$\underline{H}_2$), 5.01 (1H, d, J=4.5 Hz, 6-H), 5.27 (1H, d, J=7 Hz, a singlet by addition of D$_2$O, C$\underline{H}$CO), 5.72 (1H, d-d, J=4.5, 7.5 Hz, a doublet J=4.5 Hz by addition of D$_2$O, 7-H), 6.51 (2H, s, disappeared by addition of D$_2$O, CONH$_2$), 6.83 (1H, s, C$\underline{H}$Ph$_2$), 7.25 (15H, m, Ph-H), 9.05 (1H, d, J=7.5 Hz, disappeared by addition of D$_2$O, 7-NH).

Anal. Calculated for $C_{35}H_{36}N_4O_8S\cdot H_2O$: C, 60.86; H, 5.55; N, 8.11; S, 4.64. Found: C, 60.32; H, 5.15; N, 7.90; S, 4.71.

7-D-α-Amino-α-phenylacetamido-3-carbamoyloxymethyl-3-cephem-4-carboxylic Acid (6)

To a suspension of 5 (270 mg., 0.4 m.mol.) in 0.5 ml. of CH$_2$Cl$_2$ were added 0.4 ml. of TFA (trifluoroacetic acid) and 0.1 ml. of anisole. The mixture was stirred for 15 minutes at room temperature and evaporated to remove the TFA and CH$_2$Cl$_2$ under reduced pressure. Anhydrous ether (10 ml.) was added to the residue to produce a precipitate which was collected by filtration, washed with ether (3 × 5 ml.) and dried to afford 206 mg. (99%) of the TFA salt of 6 melting at 190° C. (gradual dec.).

ir: $\nu_{max}^{KBr}$ 3400, 3200, 3050, 1770, 1710, 1690 cm$^{-1}$.

uv: $\lambda_{max}^{pH7\ buffer}$ 260 nm ($\epsilon$ 6400).

Anal. Calculated for $C_{17}H_{18}N_4O_6S\cdot CF_3COOH$: C, 43.85; H, 3.68; N, 10.81; S, 6.16. Found: C, 43.89; H, 3.75; N, 10.13; S, 6.17.

A suspension of the TFA salt (510 mg., 0.98 m. mole) in 5 ml. of acetonitrile was adjusted with concentrated NH$_4$OH to pH 6 under vigorous stirring. The precipitate was collected by filtration and dried to afford 390 mg. (98%) of 6 melting at 190° C. (grad. dec.).

ir: $\nu_{max}^{KBr}$ 3400, 3200, 3050, 1770, 1710, 1690, 1600 cm$^{-1}$.

uv: $\lambda_{max}^{pH7\ buffer}$ 260 nm ($\epsilon$ 4900).

nmr: $\delta_{ppm}^{D_2O+NaHCO_3}$ 3.30 (2H, m, 2-H), 4.67 (2H, m, 3-CH$_2$), 4.97 (1H, d, J=4.5 Hz, 6-H), 5.13 (1H, s, C$\underline{H}$CO), 5.58 (1H, d, J=4.5 Hz, 7-H), 7.33 (5H, s, Ph-H).

Anal. Calculated for $C_{17}H_{18}N_4O_6S\cdot H_2O$: C, 48.11; H, 4.75; N, 13.20; S, 7.55. Found: C, 48.20; H, 4.76; N, 12.80; S, 7.25.

BB-S520; Sodium 7-[D-α-(4-hydroxy-1,5-naphthyridine-3-carboxamido)-α-phenylacetamido]-3-carbamoyloxymethyl-3-cephem-4-carboxylate (7)

N-Hydroxysuccinimide ester of 4-hydroxy-1,5-naphthyridine-3-carboxylic acid (U.S. Pat. No. 3,945,995, Example E) (143 mg., 0.5 m.mole) was added to a solution of 6 (203 mg., 0.5 m.mole) in 6 ml. of DMF (dimethylformamide) and 101 mg. (1 m.mole) of Et₃N. The mixture was stirred overnight at room temperature and evaporated under reduced pressure. The residue was triturated with dry acetone, filtered and dissolved in 2 ml. of DMF. To the solution was added 1 ml. of 1M sodium 2-ethylhexanoate in ethyl acetate solution and the mixture was stirred for 15 minutes and diluted with 50 ml. of acetone to separate the precipitate which was dissolved in 3 ml. of water and chromatographed on a column of resin HP-20 (15 ml.). The column was developed successively with water (500 ml.), 10% aqueous MeOH (250 ml.), 30% aqueous MeOH (120 ml.) and 50% aqueous MeOH (100 ml.). The eluate was collected in 20-ml. fractions monitoring with uv (260 nm). The fractions 30–44 were combined and evaporated to a small volume under reduced pressure and lyophilized to afford 72 mg. (32%) of BB-S520 (7). M.P. >300° C.

ir: $\nu_{max}^{KBr}$ 3400, 1770, 1710, 1690, 1660, 1610, 1530 cm$^{-1}$.

uv: $\lambda_{max}^{pH7\ buffer}$ 256 nm ($\epsilon$ 31000), 310 nm ($\epsilon$ 7400).

Anal. Calculated for $C_{26}H_{21}N_6O_8SNa \cdot 3H_2O$: C, 46.15; H, 4.02; N, 12.41; S, 4.74. Found: C, 46.10; H, 3.78; N, 12.24; S, 5.11.

EXAMPLE 2

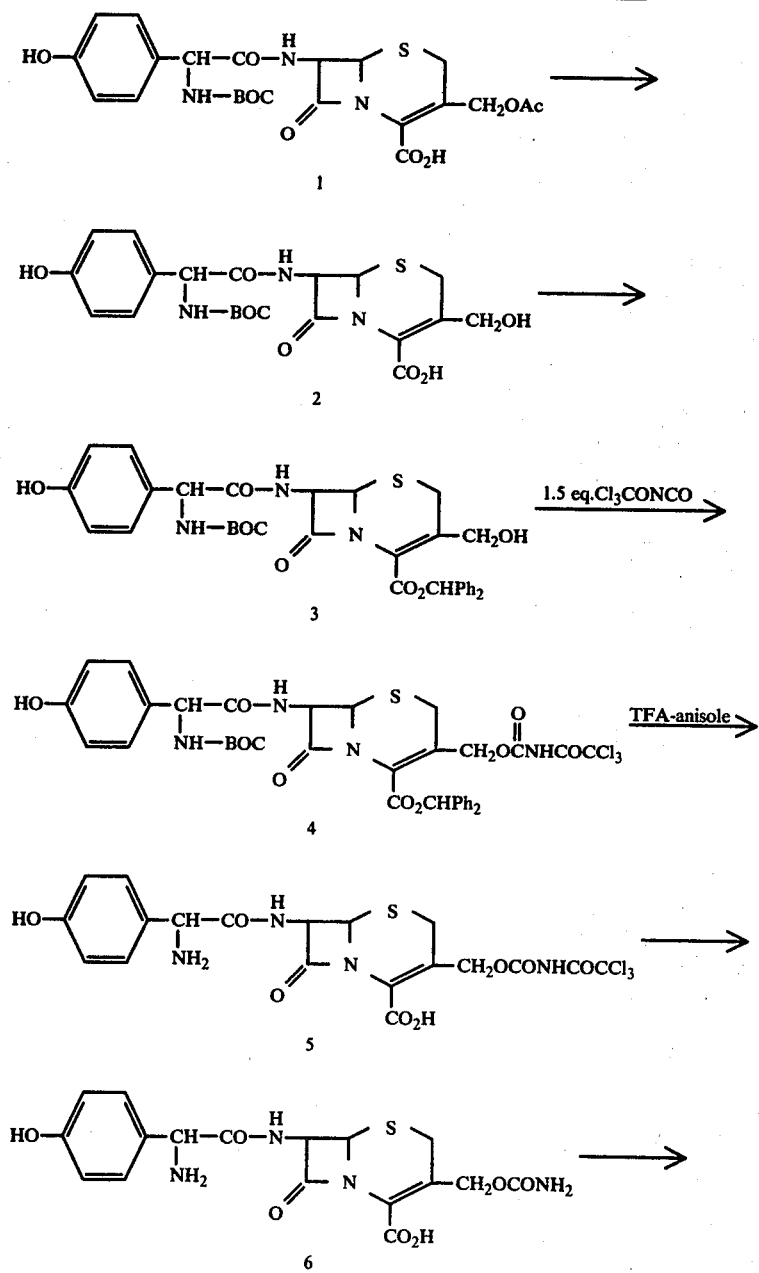

Scheme 2. Preparation of BB-S530

-continued
Scheme 2. Preparation of BB-S530

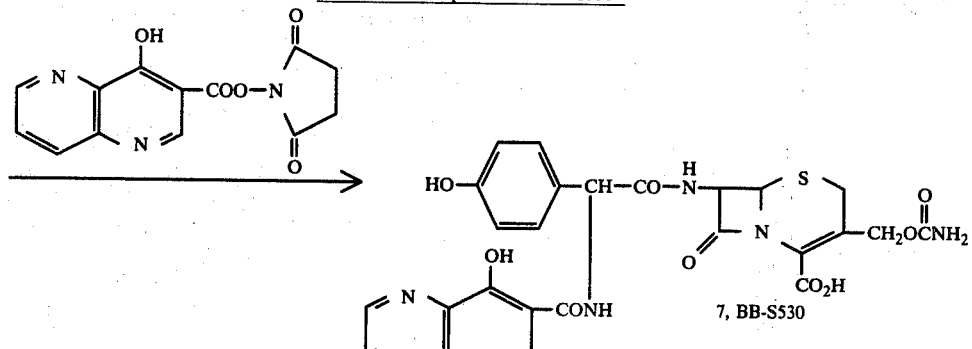

BOC represents the t-butoxycarbonyl group, Ph is phenyl and TFA is trifluoroacetic acid.

Sodium 7-[D-(-)-α-t-butoxycarbonylamino-α-(p-hydroxyphenyl) acetamido]cephalosporadesate (2)

To a suspension of 7-[D-(-)-α-t-butoxycarbonylamino- α-(p-hydroxyphenyl)acetamido]cephalosporanic acid (1, 13 g., 25 m.moles) in 100 ml. of water was added 75 ml. of N NaOH at 7° C. in one portion with stirring. The reaction mixture was allowed to stand for 45 minutes under ice-cooling, adjusted with 10% HCl to pH 8.3 and then chromatographed on a column of HP-20 (250 ml). The column was developed successively with water (2 L) and 30% aq. MeOH (2 L). The eluate was collected in 120 ml. fractions monitoring with tlc (silica gel plate, solvent system: $CH_3CN/H_2O$ = 4/1, detected with $I_2$). The fractions 8–21 were combined and evaporated to dryness to afford 5.6 g. (45%) of 2. Additional product (1.1 g.) was obtained from the fractions 4–7 which were chromatographed again with the same system above. M.p. > 190° C. (gradual dec.).

ir: $\nu_{max}^{KBr}$ 3350, 1770, 1680, 1660 cm$^{-1}$.
uv: $\lambda_{max}^{buffer(pH7)}$ 229 nm (ε, 12500), 263 nm (ε, 7300).
nmr: $\delta_{ppm}^{D_2O}$ 1.47 (9H, s, t.Bu-H), 3.22 and 3.58 (each 1H, d, J=18 Hz, 2-H), 4.20 (2H, s, 3-$CH_2$), 4.97 (1H, d, J=4.5 Hz, 6-H), 5.08 (1H, s, C$\underline{H}$CO), 5.6 (1H, d, J=4.5 Hz, 7-H), 6.87 and 7.28 (each 2H, d, J=8 Hz, benzene-H).

Anal. Calc'd. for $C_{21}H_{24}N_3O_8SNa \cdot 2H_2O$: C, 46.92; H, 5.25; N, 7.82; S, 5.96. Found: C, 47.27; H, 4.74; N, 7.48; S, 5.64.

Benzhydryl 7-[D-(-)-α-t-butoxycarbonylamino-α-(p-hydroxyphenyl)acetamido]cephalosporadesate (3)

A solution of 2 (800 mg., 1.6 m.mole) in 5 ml. of water was layered with 10 ml. AcOEt (ethylacetate), cooled to 0° C. and adjusted to pH 2 with 10% HCl under stirring. The AcOEt layer was separated and the aqueous layer was extracted with 20 ml. of AcOEt. The extracts were combined, washed with saturated aqueous NaCl (2 × 10 ml.) and dried over $MgSO_4$. To the extracts was added a solution of diphenyldiazomethane (about 8 m.moles) in AcOEt (10 ml.) at 0–5° C. with stirring. The reaction mixture was stirred for 4 hours at room temperature and evaporated to dryness under reduced pressure. The residue was washed with n-hexane (3 × 20 ml.), dissolved in THF (5ml.) and filtered to remove insolubles. The filtrate was diluted with n-hexane (100 ml.) and the resulting precipitate was collected by filtration to afford 1.05 g. (100%) of 3 melting at 129–134° C. (dec.).

ir: $\nu_{max}^{KBr}$ 3400, 1785, 1710, 1680 cm$^{-1}$.
uv: $\lambda_{max}^{EtOH}$ 220 nm (ε, 25800), 259 nm (ε, 9500).
nmr: $\delta_{ppm}^{DMSO-d_6}$ 1.37 (9H, s, t.Bu-H), 3.48 (2H, br-s, 2-H), 4.12 (2H, d, J=5 Hz, a singlet by $D_2O$, 3-C$\underline{H}_3$), 4.95 (1H, d, J=4.5 Hz, 6-H), 5.05 (1H, t, J=5 Hz, disappeared by $D_2O$, $CH_2O\underline{H}$), 5.15 (1H, d, J=6 Hz, a singlet by $D_2O$, C$\underline{H}$CO), 5.67 (1H, d-d, J=4.5, 7.5 Hz, a doublet J=4.5 Hz by $D_2O$, 7-H), 6.57 (2H, d, J=8 Hz, benzene-H), 6.77 (1H, s, C$\underline{H}$-Ph$_2$), 7.2 (12H, m, Ph-H), 8.93 (1H, d, J=7.5 Hz, disappeared by $D_2O$, 7-N$\underline{H}$), 9.2 (1H, s, disappeared by $D_2O$, Ph-O$\underline{H}$).

Anal. Calc'd for $C_{34}H_{35}N_3O_8S$: C, 63.24; H, 5.46; N, 6.51; S, 4.97. Found: C, 63.59; H, 5.89; N, 5.77; S, 4.69.

Benzhydryl 7-[D-(-)-α-t-butoxycarbonylamino-α-(p-hydroxyphenyl)acetamido]-3-trichloroacetylcarbamoyloxymethyl-3-cephem-4-carboxylate (4)

A solution of trichloroacetylisocyanate (1.74 g., 9.2 m.moles) in 2 ml. of dry acetone was added to a solution of 3 (4.2 g., 6.5 m.moles) in 10 ml. of dry acetone at −5° to 0° C. with stirring over a period of 15 minutes. The mixture was stirred at 0° to 5° C. for 3 hours and diluted with 100 ml. of n-hexane below 10° C. to separate the precipitate, which was collected by filtration, washed with n-hexane and dried to afford 5.5 g. (100%) of 4 melting at > 132° C. (gradual dec.).

ir: $\nu_{max}^{KBr}$ 3400, 1790, 1730, 1690 cm $^{-1}$.
uv: $\lambda_{max}^{EtOH}$ 220 nm (ε, 23000), 259 nm (ε, 8300).
nmr: $\delta_{ppm}^{DMSO-d_6}$ 1.37 (9H, s, t.Bu-H), 3.53 (2H, br-s, 2-H), 4.8 (2H, br-s, 3-$CH_2$), 5.0 (1H, d, J=4.5 Hz, 6-H), 5.12 (1H, d, J=7 Hz, a singlet by $D_2O$, C$\underline{H}$CO), 5.55 (1H, d-d, J=4.5, 7.5 Hz, a doublet, J=4.5 Hz by $D_2O$, 7-H), 6.57 (2H, d, J=8 Hz, benzene-H), 6.8 (1H, s, C$\underline{H}$-Ph$_2$), 7.18 (12H, m, benzene-H), 8.18 (1H, m, disappeared by $D_2O$, Ph.OH), 8.88 (1H, d, J=7.5 Hz, disappeared by $D_2O$, 7-NH), 11.6 (1H, s, disappeared by $D_2O$, N$\underline{H}$COCCl$_3$).

Anal. Calc'd for $C_{37}H_{35}N_4O_{10}SCl_3 \cdot H_2O$: C, 52.15; H, 4.38; N, 6.57; S, 3.76. Found: C, 52.47; H, 4.37; N, 6.26; S, 3.36.

7-[D-(-)-α-Amino-α-(p-hydroxyphenyl)acetamido]-3-trichloroacetylcarbamoyloxymethyl-3-cephem-4-carboxylic Acid (5)

A mixture of 4 (5.4 g., 6.5 m. moles), 1 ml. of anisole and 20 ml. of TFA was stirred for 30 minutes at room temperature and concentrated to a small volume under reduced pressure. Anhydrous ether (50 ml.) was added to the residue to separate the precipitate, which was collected by filtration, washed with ether (3 × 10 ml.) and dried to afford 4.1 g. (92%) of the trifluoroacetate of 5 melting at >150° (gradual dec.).

ir: $\nu_{max}^{KBr}$ 3400, 3200, 1785, 1690, 1680 cm$^{-1}$.

uv: $\lambda_{max}^{buffer\,(pH\,7)}$ 228 nm ($\epsilon$, 15200), 260 nm ($\epsilon$,6700).

nmr: $\delta_{ppm}^{DMSO-d_6}$ 3.57 (2H, br-s, 2-H), 4.95 (3H, m, 6-H and 3-CH$_2$), 5.33 (1H, m, C$\underline{H}$CO), 5.65 (1H, m, a doublet J=4.5 Hz by D$_2$O, 7-H), 6.65 and 7.18 (each 2H, d, J=8 Hz, benzene-H), 8.33 (2H, m, disappeared by D$_2$O), 9.28 (1H, d, J=7.5 Hz disappeared by D$_2$O, 6-N$\underline{H}$).

7-[D-(-)-α-Amino-α-(p-hydroxyphenyl)acetamido]-3-carbamoyloxymethyl-3-cephem-4-carboxylic Acid (6)

A mixture of the trifluoroacetate of 5 (340 mg., 0.5 m.mole) and Na$_2$CO$_3$ (106 mg., 1 m.mole) in 5 ml. of 10% aqueous MeOH (methanol) was stirred for 45 minutes at room temperature, diluted with 5 ml. of water, adjusted to pH 8.5 with 10% HCl, evaporated to remove MeOH under reduced pressure and chromatographed on a column of HP-20 (80 ml.). The column was developed successively with water (300 ml.) and 30% MeOH (1 L.). The eluate was collected in 20 ml. fractions, monitoring with uv (260 nm( and tlc (silica gel plate, solvent system: CH$_3$CN/H$_2$O = 4/1, detected with ninhydrin). The fractions 16–30 were combined, evaporated to a small volume and lyophilized to afford 150 mg. (71%) of 6. M.p. >200° (gradual dec.).

ir: $\nu_{max}^{KBr}$ 3400, 3200, 1775, 1710, 1690 cm$^{-1}$.

uv: $\lambda_{max}^{buffer\,(pH\,7)}$ 229 nm ($\epsilon$, 14100), 263 nm ($\epsilon$, 6500).

nmr: $\delta_{ppm}^{D_2O+NaHCO_3}$ 3.07 and 3.48 (each 1H, d, J=20 Hz, 2-H), 4.61 (2H, br-s, 3-C$\underline{H}_2$), 4.88 (1H, s, C$\underline{H}$CO), 4.92 (1H, d, J=4.5 Hz, 6-H), 5.58 (1H, d, J=4.5 Hz, 7-H), 6.85 and 7.28 (each 2H, d, J=7 Hz, benzene-H).

Anal. Calc'd for C$_{17}$H$_{18}$N$_4$O$_7$S.H$_2$CO$_3$: C, 44.63; H, 4.16; N, 11.57; S, 6.62. Found: C, 44.57; H, 4.08; N, 11.34; S, 6.95.

BB-S530; Sodium 7-[D-(-)-α-(4-hydroxy-1,5-naphthyridine-3-carboxamido)-α-(p-hydroxyphenyl)acetamido]-3-carbamoyloxymethyl-3-cephem-4-carboxylate (7)

N-Hydroxysuccinimido ester of 4-hydroxy-1,5-naphthyridine-3-carboxylic acid (430 mg., 1.5 m.mole) was added to a solution of 6 (422 mg., 1 m.mole) in 6 ml. of DMF (dimethylformamide) and 253 mg. (2.5 m.moles) of Et$_3$N. The mixture was stirred overnight at room temperature and concentrated to a small volume under reduced pressure. The residue was triturated with dry acetone and dissolved in 3 ml. of DMF. To the solution was added 2 ml. of 1 M sodium 2-ethylhexanoate in AcOEt solution. The mixture was stirred for 15 minutes, evaporated to a small volume and diluted with 150 ml. of acetone to separate the precipitate which was dissolved in 5 ml. of water and chromatographed on a column of HP-20 (40 ml.). The column was developed successively with water (300 ml.), 10% aq. MeOH (100 ml.) and 30% aq. MeOH (500 ml.). The eluate was collected in 20 ml. fractions monitoring with uv (260 nm) and tlc (silica gel plate, CH$_3$CN/H$_2$O = 4/1, detected with I$_2$, Rf = 0.2). The fractions 21–31 were combined and concentrated under reduced pressure. The residue was diluted with 30 ml. of dry acetone to separate the precipitate which was collected by filtration and dried to afford 205 mg. (34%) of BB-S530 melting at >250° (gradual dec.).

ir: $\nu_{max}^{KBr}$ 3400, 3250, 1765, 1650, 1610, 1520 cm$^{-1}$.

uv: $\lambda_{max}^{buffer\,(pH\,7)}$ 228 nm ($\epsilon$, 22900), 255 nm ($\epsilon$, 32800), 310 nm ($\epsilon$, 8040).

Anal. Calc'd for C$_{26}$H$_{21}$N$_6$O$_9$SNa.3H$_2$O: C, 46.57; H, 4.06; N, 12.53; S, 4.78. Found: C, 46.94; H, 3.63; N, 12.09; S, 4.75.

Biological Activity (Tables 1 and 2)

Minimum inhibitory concentrations (MIC) of BB-S520 were determined by serial two-fold agar dilution method using Steers' apparatus on Meuller-Hinton agar plate against 31 test organisms for the primary screening and also against 61 strains of *Pseudomonas aeruginosa* for the secondary evaluation. The results are shown in Table 1 and Table 2 along with those of BB-S514 and sulbenicillin.

The following table shows mean % relative activity of BB-S520 and BB-S514 to sulbenicillin which was calculated from geometric means (GM) of MIC's in Table 1 and Table 2.

Mean % relative activity = $\dfrac{\text{GM of MIC's of sulbenicillin}}{\text{GM of MIC's of test compound}} \times 100$ Mean % Relative Activity (Sulbenicillin = 100%)

|  | Organisms | BB-S520 | BB-S514 | Sulbenicillin |
|---|---|---|---|---|
| Table 1 | Pseudomonas (6 strains) | 635 | 283 | 100 |
|  | Gram-negative (19 strains) | 179 | 96 | 100 |
|  | Gram-positive (6 strains) | 200 | 71 | 100 |
| Table 2 | Ps. aeruginosa (61 strains) | 714 | 480 | 100 |

BB-S514 has the structure

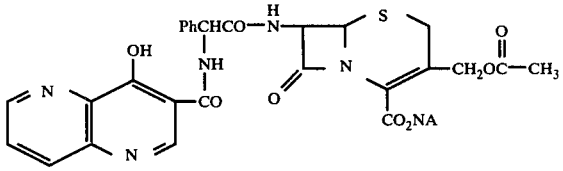

BB-S514

Table 1

In vitro Activity of BB-S514 and BB-S520 by Agar Dilution Technique (Mueller-Hinton Agar)

| | MIC (Mcg./Ml.) | | |
|---|---|---|---|
| Organisms | BB-S514 | BB-S520 | Sulbenicillin |
| S. aureus Smith | 3.1 | 0.8 | 1.6 |
| S. aureus Smith | 6.3 | 1.6 | 6.3 |
| S. aureus BX-1633 | 3.1 | 0.8 | 3.1 |
| S. aureus | 25 | 25 | 25 |
| S. aureus | 6.3 | 1.6 | 3.1 |
| S. aureus | >100 | 50 | 50 |
| E. coli NIHJ | 0.1 | 0.05 | 0.8 |
| E. coli Juhl | 12.5 | 1.6 | 1.6 |
| E. coli | 0.4 | | 0.8 |
| E. coli | 0.4 | 0.8 | 1.6 |
| E. coli | >100 | 100 | >100 |
| E. coli | 6.3 | 3.1 | 6.3 |
| E. coli | >100 | 100 | >100 |
| E. coli | 12.5 | 3.1 | >100 |
| E. coli | 0.8 | 0.4 | 6.3 |
| K. pneumoniae | 6.3 | 1.6 | 6.3 |
| Klebsiella sp. | 12.5 | 3.1 | 12.5 |
| E. cloacae | 25 | 12.5 | 12.5 |
| E. cloacae | 50 | 50 | >100 |
| E. cloacae | 25 | 25 | 12.5 |

Table 1-continued

In vitro Activity of BB-S514 and BB-S520 by Agar Dilution Technique (Mueller-Hinton Agar)

| Organisms | MIC (Mcg./Ml.) | | |
|---|---|---|---|
| | BB-S514 | BB-S520 | Sulbenicillin |
| P. mirabilis | 0.8 | 0.4 | 0.8 |
| P. vulgaris | 25 | 100 | 3.1 |
| P. morganii | >100 | >100 | >100 |
| S. enteritidis | 6.3 | 3.1 | 1.6 |
| S. marcescens | >100 | >100 | 6.3 |
| P. aeruginosa | 3.1 | 1.6 | 12.5 |
| P. aeruginosa | 3.1 | 3.1 | 25 |
| P. aeruginosa | 6.3 | 3.1 | 25 |
| P. aeruginosa | 25 | 12.5 | 100 |
| P. aeruginosa | 6.3 | 1.6 | 12.5 |
| P. aeruginosa | 3.1 | 1.6 | 3.1 |

Table 2

Minimum Inhibitory Concentration (MIC, mcg./ml.) of BB-S514 and BB-S520 against 61 Strains of Pseudomonas aeruginosa (Mueller-Hinton Agar)

| BBRI Pa-No. | Organism | MIC (mcg./ml.) | | |
|---|---|---|---|---|
| | | BB-S514 | BB-S520 | Sulbenicillin |
| 1 | P. aeruginosa D15 | 6.3 | 12.5 | 25 |
| 2 | P. aeruginosa VA | 6.3 | 3.1 | 12.5 |
| 3 | P. aeruginosa 1449VA | 3.1 | 1.6 | 6.3 |
| 4 | P. aeruginosa H9 D113 | 12.5 | 12.5 | 25 |
| 5 | P. aeruginosa M4865KC | 6.3 | 3.1 | 25 |
| 6 | P. aeruginosa No. 5 | 25 | 25 | >100 |
| 7 | P. aeruginosa | 12.5 | 6.3 | 25 |
| 8 | P. aeruginosa | 6.3 | 3.1 | 25 |
| 9 | P. aeruginosa Yale | 6.3 | 3.1 | 25 |
| 10 | P. aeruginosa | 50 | 50 | >100 |
| 11 | P. aeruginosa | 6.3 | 3.1 | 25 |
| 12 | P. aeruginosa | 6.3 | 6.3 | 50 |
| 14 | P. aeruginosa | 6.3 | 3.1 | 25 |
| 15 | P. aeruginosa | 12.5 | 12.5 | 100 |
| 16 | P. aeruginosa No. 130 | 1.6 | 0.8 | 6.3 |
| 17 | P. aeruginosa H6 D114 | 3.1 | 6.3 | 12.5 |
| 18 | P. aeruginosa H8 D121 | 6.3 | 6.3 | 12.5 |
| 19 | P. aeruginosa | 3.1 | 1.6 | 12.5 |
| 20 | P. aeruginosa | 6.3 | 3.1 | 25 |
| 21 | P. aeruginosa | 6.3 | 3.1 | 25 |
| 23 | P. aeruginosa | 6.3 | 6.3 | 50 |
| 24 | P. aeruginosa | 50 | 50 | 100 |
| 25 | P. aeruginosa | 1.6 | 1.6 | 12.5 |
| 26 | P. aeruginosa Ps32 | 3.1 | 3.1 | 12.5 |
| 27 | P. aeruginosa GN315 | 6.3 | 3.1 | 50 |
| 28 | P. aeruginosa CPH10527/72 | 6.3 | 6.3 | 50 |
| 29 | P. aeruginosa D122 | 3.1 | 1.6 | 25 |
| 30 | P. aeruginosa | 6.3 | 3.1 | 25 |
| 31 | P. aeruginosa | 1.6 | 1.6 | 12.5 |
| 32 | P. aeruginosa | 6.3 | 3.1 | 25 |
| 33 | P. aeruginosa | 25 | 12.5 | 100 |
| 34 | P. aeruginosa | 6.3 | 3.1 | 25 |
| 35 | P. aeruginosa | 25 | 12.5 | 100 |
| 36 | P. aeruginosa | 0.4 | 0.4 | 1.6 |
| 37 | P. aeruginosa | 6.3 | 3.1 | 50 |
| 38 | P. aeruginosa | 12.5 | 6.3 | 50 |
| 39 | P. aeruginosa | 3.1 | 3.1 | 25 |
| 41 | P. aeruginosa | 6.3 | 3.1 | 25 |
| 42 | P. aeruginosa | 12.5 | 6.3 | >100 |
| 43 | P. aeruginosa | 6.3 | 6.3 | 50 |
| 44 | P. aeruginosa | 6.3 | 6.3 | 50 |
| 45 | P. aeruginosa GN4925 | 12.5 | 6.3 | 50 |
| 51 | P. aeruginosa | 6.3 | 3.1 | 25 |
| 52 | P. aeruginosa | 6.3 | 3.1 | 25 |
| 53 | P. aeruginosa | 6.3 | 3.1 | 25 |

Table 2-continued

Minimum Inhibitory Concentration (MIC, mcg./ml.) of BB-S514 and BB-S520 against 61 Strains of Pseudomonas aeruginosa (Mueller-Hinton Agar)

| BBRI Pa-No. | Organism | MIC (mcg./ml.) | | |
|---|---|---|---|---|
| | | BB-S514 | BB-S520 | Sulbenicillin |
| 54 | P. aeruginosa | 6.3 | 3.1 | 50 |
| 55 | P. aeruginosa | 6.3 | 3.1 | 25 |
| 56 | P. aeruginosa | 6.3 | 3.1 | 25 |
| 57 | P. aeruginosa | 3.1 | 3.1 | 25 |
| 58 | P. aeruginosa | 12.5 | 6.3 | 50 |
| 59 | P. aeruginosa | 6.3 | 6.3 | 50 |
| 60 | P. aeruginosa | 3.1 | 3.1 | 12.5 |
| 61 | P. aeruginosa | 6.3 | 6.3 | 50 |
| 62 | P. aeruginosa | 12.5 | 6.3 | >100 |
| 64 | P. aeruginosa | 6.3 | 3.1 | 25 |
| 65 | P. aeruginosa | 3.1 | 3.1 | 25 |
| 66 | P. aeruginosa | 3.1 | 3.1 | 25 |
| 67 | P. aeruginosa | 12.5 | 6.3 | 50 |
| 68 | P. aeruginosa | 12.5 | 6.3 | 50 |
| 69 | P. aeruginosa | 25 | 12.5 | 50 |
| 70 | P. aeruginosa K-Ps102 (CR-102) | 6.3 | 3.1 | 25 |

Table 3

Mouse Blood Levels

| Dose in Mgm./Kg. | Compound | Blood Levels in Mcg./Ml. at Indicated Hours After Subcutaneous Injection | | | |
|---|---|---|---|---|---|
| | | 0.25 | 0.5 | 1.0 | 2.0 |
| 40 | BB-S520 | 25 | 20 | 7 | 1 |
| 40 | Sulbenicillin | 22 | 14 | 5 | <1 |
| 20 | BB-S520 | 13 | 9 | 3.7 | — |
| 20 | Sulbenicillin | 9.8 | 7.5 | 1.2 | — |

Table 4

Median Curative Dose in Mgm./Kg. Upon Subcutaneous Injection in Mice

| | $PD_{50}$ in Mgm./Kg. | |
|---|---|---|
| | Compound | |
| Organism | BB-S520 | Sulbenicillin |
| S. aureus Smith | 0.8 | 2.4 |
| E. coli Juhl | 1.8 | 9.5 |
| Ps. aeruginosa | 37 | 85 |

Biological Acitivity (Tables 5, 6 and 7)

Minimum inhibitory concentrations (MIC) of cephalosporins in the present study were determined by serial two-fold agar dilution method using Steers' apparatus on Mueller-Hinton agar plate against 31 test organisms for the primary screening and also against 61 strains of Pseudomonas aeruginosa for the secondary evaluation.

Table 5 shows the in vitro activity of these cephalosporins in terms of mean percent relative activity of MIC to sulbenicillin (SBPC) along with $PD_{50}$ values against infections with S. aureus Smith, E. coli Juhl and Ps. aeruginosa A9843.

Tables 6 and 7 show MIC values of BB-S530 and reference compounds in the primary and secondary evaluations, respectively.

Table 5
Anti-pseudomonal Cephalosporins with 3-Carbamoyloxymethyl Side Chain

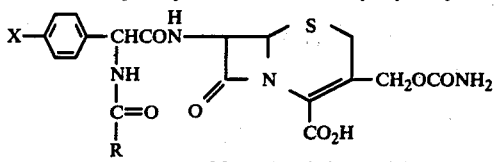

| Code No. | X | R | Mean % Relative Activity (SPBC = 100%) G(+) (6)* | G(−) (19) | P. aerug. (6) | P. aerug. (61) | PD$_{50}$ (mg./kg., mice) S. aureus Smith | E. coli Juhl | P. aerug. A9843 |
|---|---|---|---|---|---|---|---|---|---|
| BB-S520 | H | (naphthyridinyl-OH) | lot 1 200 lot 2 141 | 179 108 | 635 712 | 714 1016 | 0.8 | 1.8 | 37 |
| BB-S530 | HO | (naphthyridinyl-OH) | 141 | 108 | 1425 | 1694 | 1.3 | 1.8 | 9.3 |
| Sulbenicillin | | | 100 | 100 | 100 | 100 | 2.4 | 9.5 8.5 | 140 130 |

*Figures in parentheses indicate numbers of strains tested.

Table 6
In vitro Activity of BB-S530 by Agar Dilution Technique (Mueller-Hinton Agar)

| Organism | | BB-S530 | Carbenicillin | Sulbenicillin |
|---|---|---|---|---|
| S. aureus Smith | A9537 | 1.6 | 0.2 | 3.1 |
| S. aureus Smith | A20239 | 3.1 | 3.1 | 6.3 |
| S. aureus BX-1633 | A9606 | 3.1 | 3.1 | 3.1 |
| S. aureus Smith | A15907 | 25 | 25 | 12.5 |
| S. aureus Smith | A20240 | 3.1 | 6.3 | 6.3 |
| S. aureus Smith | A20701 | 25 | 25 | 50 |
| E. coli NIHJ | | 1.6 | 0.4 | 0.8 |
| E. coli Juhl | A15119 | 1.6 | 1.6 | 3.1 |
| E. coli | A9844 | 0.4 | 0.2 | 0.8 |
| E. coli | A10664 | 0.2 | 0.8 | 1.6 |
| E. coli | A20366 | >100 | >100 | >100 |
| E. coli | A9435 | 3.1 | 6.3 | 12.5 |
| E. coli | A20898 | 100 | >100 | >100 |
| E. coli | A20732 | 3.1 | 100 | 100 |
| E. coli | A20520 | 3.1 | 3.1 | 6.3 |
| K. pneumoniae | A9977 | 1.6 | 3.1 | 3.1 |
| Klebsiella sp. | A20452 | 1.6 | 6.3 | 12.5 |
| E. cloacae | A9656 | 12.5 | 3.1 | 12.5 |
| E. cloacae | A9657 | 100 | 12.5 | >100 |
| E. cloacae | A9659 | 100 | 3.1 | 12.5 |
| P. mirabilis | A9900 | 6.3 | 0.4 | 0.8 |
| P. vulgaris | A9539 | >100 | 3.1 | 3.1 |
| P. morganii | A9553 | >100 | >100 | >100 |
| S. enteritidis | A9531 | 0.8 | 0.8 | 1.6 |
| S. marcescens | A20019 | >100 | 3.1 | 6.3 |
| P. aeruginosa | A9930 | 0.8 | 25 | 25 |
| P. aeruginosa | A15150 | 1.6 | 12.5 | 12.5 |
| P. aeruginosa | A9843 | 1.6 | 25 | 25 |
| P. aeruginosa | A20717 | 3.1 | 100 | 100 |
| P. aeruginosa | A20229 | 1.6 | 12.5 | 12.5 |
| Pseudomonas sp. | A20358 | 0.4 | 6.3 | 3.1 |

Table 7
Minimum Inhibitory Concentrations (MIC, mcg./ml.) of BB-S520, BB-S530 and Reference Compounds Against 61 Strains of Pseudomonas Aeruginosa (Mueller-Hinton Agar)

| BBRI Pa-No. | Organism | BB-S520 | BB-S530 | Sulbenicillin | Toyama's T-1220* |
|---|---|---|---|---|---|
| 1 | P. aerug. D15 | 6.3 | 6.3 | 12.5 | 12.5 |
| 2 | P. aerug. VA | 3.1 | 1.6 | 25 | 3.1 |
| 3 | P. aerug. 1449VA | 0.8 | 0.8 | 12.5 | 1.6 |
| 4 | P. aerug. H9 D113 | 1.6 | 1.6 | 12.5 | 3.1 |
| 5 | P. aerug. N4865KC | 0.8 | 1.6 | 6.3 | 1.6 |
| 6 | P. aerug. No. 5 | 12.5 | 6.3 | 100 | 25 |
| 7 | P. aerug. | 3.1 | 1.6 | 25 | 3.1 |
| 8 | P. aerug. | 3.1 | 1.6 | 25 | 3.1 |
| 9 | P. aerug. Yale | 1.6 | 1.6 | 12.5 | 3.1 |
| 10 | P. aerug. | 25 | 100 | >100 | >100 |
| 11 | P. aerug. | 3.1 | 1.6 | 25 | 3.1 |
| 12 | P. aerug. | 3.1 | 1.6 | 25 | 6.3 |
| 14 | P. aerug. | 0.8 | 0.8 | 12.5 | 1.6 |
| 15 | P. aerug. | 6.3 | 3.1 | 50 | 6.3 |
| 16 | P. aerug. No. 130 | 0.4 | <0.2 | 3.1 | 0.8 |
| 17 | P. aerug. H6 D114 | 3.1 | 12.5 | 25 | 25 |
| 18 | P. aerug. H8 D121 | 1.6 | 0.4 | 3.1 | 50 |
| 19 | P. aerug. | 0.8 | 0.4 | 6.3 | 0.8 |
| 20 | P. aerug. | 3.1 | 1.6 | 25 | 6.3 |
| 21 | P. aerug. | 3.1 | 1.6 | 25 | 3.1 |
| 23 | P. aerug. | 1.6 | 1.6 | 25 | 3.1 |
| 24 | P. aerug. | 25 | 50 | >100 | >100 |
| 25 | P. aerug. | 0.8 | 0.8 | 6.3 | 1.6 |
| 26 | P. aerug. Ps32 | 6.3 | 6.3 | 12.5 | 1.6 |
| 27 | P. aerug. GN315 | 1.6 | 0.4 | 12.5 | 3.1 |

Table 7-continued

Minimum Inhibitory Concentrations (MIC, mcg./ml.) of BB-S520, BB-S530 and Reference Compounds Against 61 Strains of Pseudomonas Aeruginosa (Mueller-Hinton Agar)

| BBRI Pa-No. | Organism | MIC, mcg./ml. BB-S520 | BB-S530 | Sulbenicillin | Toyama's T-1220* |
|---|---|---|---|---|---|
| 28 | P. aerug. CPH1C527/72 | 3.1 | 1.6 | 50 | 6.3 |
| 29 | P. aerug. D122 | 1.6 | 0.8 | 25 | 3.1 |
| 30 | P. aerug. | 1.6 | 0.8 | 25 | 6.3 |
| 31 | P. aerug. | 0.8 | <0.2 | 3.1 | 1.6 |
| 32 | P. aerug. | 1.6 | 0.8 | 25 | 3.1 |
| 33 | P. aerug. | 1.6 | 0.8 | 25 | 6.3 |
| 34 | P. aerug. | 1.6 | 0.4 | 12.5 | 3.1 |
| 35 | P. aerug. | 6.3 | 1.6 | 50 | 6.3 |
| 36 | P. aerug. | <0.2 | <0.2 | 0.8 | 0.4 |
| 37 | P. aerug. | 3.1 | 1.6 | 25 | 3.1 |
| 38 | P. aerug. | 6.3 | 3.1 | 100 | 6.3 |
| 39 | P. aerug. | 1.6 | 0.8 | 25 | 1.6 |
| 41 | P. aerug. | 3.1 | 1.6 | 25 | 3.1 |
| 42 | P. aerug. | 1.6 | 1.6 | >100 | 25 |
| 43 | P. aerug. | 3.1 | 1.6 | 25 | 6.3 |
| 44 | P. aerug. | 3.1 | 1.6 | 50 | 3.1 |
| 44 | P. aerug. GN4925 | 6.3 | 1.6 | 50 | 6.3 |
| 51 | P. aerug. | 1.6 | 0.8 | 25 | 3.1 |
| 52 | P. aerug. | 3.1 | 1.6 | 50 | 3.1 |
| 53 | P. aerug. | 1.6 | 0.8 | 25 | 3.1 |
| 54 | P. aerug. | 1.6 | 0.8 | 25 | 3.1 |
| 55 | P. aerug. | 3.1 | 1.6 | 25 | 3.1 |
| 56 | P. aerug. | 3.1 | 1.6 | 25 | 3.1 |
| 57 | P. aerug. | 1.6 | 0.8 | 25 | 6.3 |
| 58 | P. aerug. | 3.1 | 1.6 | 50 | 6.3 |
| 59 | P. aerug. | 1.6 | 0.8 | 25 | 1.6 |
| 60 | P. aerug. | 1.6 | 0.8 | 12.5 | 3.1 |
| 61 | P. aerug. | 1.6 | 1.6 | 25 | 3.1 |
| 62 | P. aerug. | 50 | 100 | >100 | 12.5 |
| 64 | P. aerug. | 3.1 | 1.6 | 25 | 3.1 |
| 65 | P. aerug. | 1.6 | 1.6 | 25 | 1.6 |
| 66 | P. aerug. | 1.6 | 0.8 | 25 | 3.1 |
| 67 | P. aerug. | 3.1 | 1.6 | 25 | 6.3 |
| 68 | P. aerug. | 3.1 | 1.6 | 50 | 6.3 |
| 69 | P. aerug. | 6.3 | 3.1 | 100 | 6.3 |
| 70 | P. aerug.K-Ps102(CR-102) | 1.6 | 0.8 | 50 | 3.1 |
| Geometric Mean of MIC | | 2.4 | 1.4 | 24 | 4.3 |
| Rel. Act. (SBPC=100%) | | 1016 | 1694 | 100 | 544 |

*Toyama's T-1220 is a penicillin of the formula

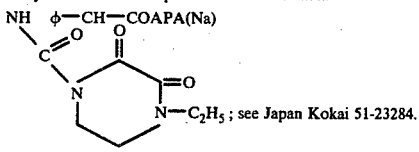

; see Japan Kokai 51-23284.

There is also provided by the present invention a compound having the formula

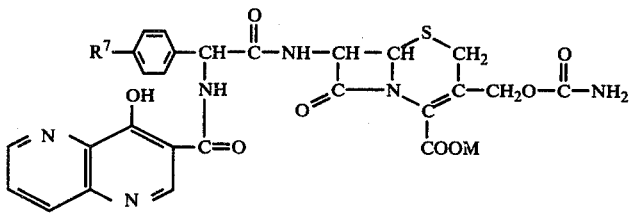

wherein $R^7$ is hydrogen or hydroxy and M is

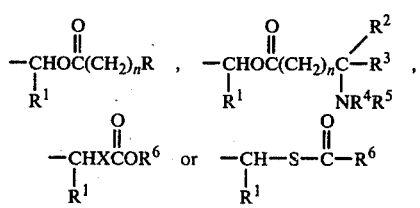

n is 0 to 4; R is hydrogen, alkyl having 1 to 8 carbon atoms, cycloalkyl of 3 to 6 carbon atoms, phenyl, $C_1$-$C_4$ phenalkyl, pyridyl, thienyl, or pyrrolyl; $R^1$ is hydrogen, methyl or ethyl; $R^2$ and $R^3$ are each hydrogen, alkyl having 1 to 6 carbon atoms, phenyl, pyridyl, or thienyl; $R^4$ and $R^5$ are each hydrogen or alkyl of 1 to 4 carbon atoms; $R^6$ is alkyl having 1 to 4 carbon atoms, pheny, phenalkyl having 1 to 4 carbon atoms, pyridyl, thiadiazolyl, amino or $C_1$-$C_4$ alkylamino; X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR^1$, $N(R^1)_2$, nitro, fluoro, chloro, bromo, or carboxy.

There is also provided by the present invention a compound having the formula

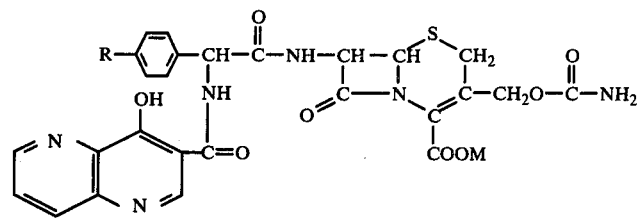

wherein R is hydrogen or hydroxy and M is selected from the group consisting of

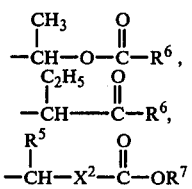

wherein $R^5$ is a hydrogen atom, a methyl or an ethyl group; $X^2$ is —O—, —NH—; $R^6$ is a basic group such as alkyl or aralkyl substituted with substituted or unsubstituted $NH_2$, such as alkyl-$NHCH_3$, aralkyl-$NHCH_3$,

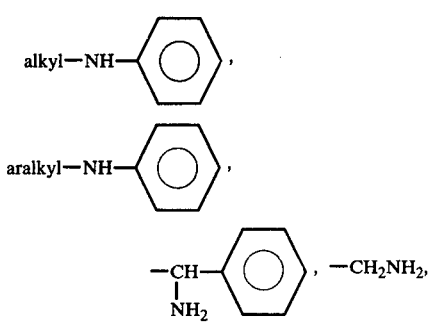

$R^7$ is an alkyl group such as a methyl, ethyl, propyl, isopropyl, butyl, isobutyl, pentyl or 2-ethyl-hexyl group; a cycloalkyl group such as cyclopropyl, cyclobutyl, cyclopentyl, cyclohexyl or cycloheptyl; an aryl group such as phenyl or naphthyl; an aralkyl group such as benzyl or naphthylmethyl; a heterocyclic group and wherein the alkyl, cycloalkyl, aryl, aralkyl and heterocyclic groups may be substituted with one or more groups selected from the class consisting of amino groups, substituted amino groups such as methylamino, diethylamino or acetamido groups, the halogen groups such as fluorine, chlorine or bromine, nitro groups, alkoxy groups such as methoxy, ethoxy, propyloxy, isopropyloxy, butoxy or isobutoxy.

There is also provided by the present invention a compound having the formula

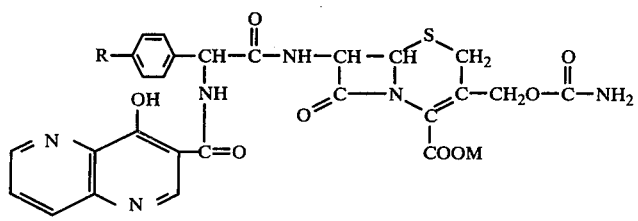

wherein R is hydrogen or hydroxy and M is

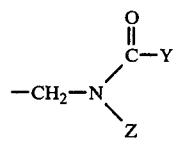

wherein Y is alkyl of one to six carbon atoms, phenyl, benzyl, alkoxy of one to six carbon atoms, or benzyloxy; Z is alkyl of one to six carbon atoms, phenylbenzyl, alkoxy of one to six carbon atoms, cyclopentyl, cyclohexyl and phenyl, or Y+Z taken together are a 3-benzoxazolidine ring.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

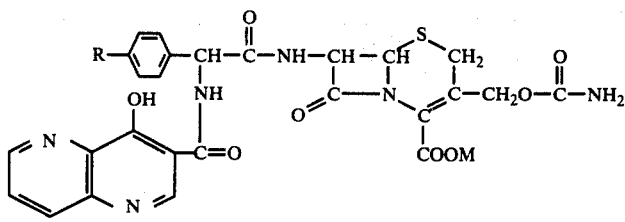

wherein R is hydrogen or hydroxy and M is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl and preferably is hydrogen.

There is further provided by the present invention a method of treating bacterial infections comprising administering by injection to an infected warm-blooded animal, including man, an effective but nontoxic dose of 250–1000 mgm. of a compound having the formula

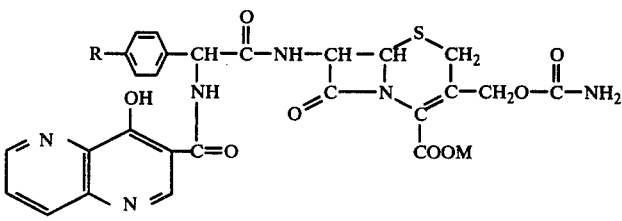

wherein R is hydrogen or hydroxy and M is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl or a nontoxic, pharmaceutically acceptable salt thereof.

There is also provided by the present invention a method for combatting *Pseudomonas aeruginosa* infections which comprises administering to a warm-blooded mammal infected with a *Pseudomonas aeruginosa* infection an amount effective for treating said *Pseudomonas aeruginosa* infection of a composition comprising a compound having the formula

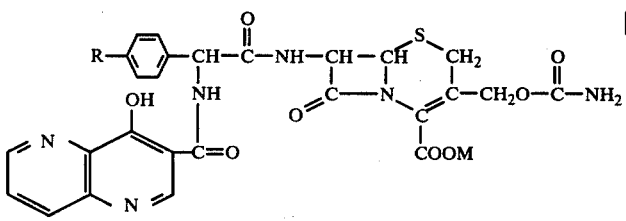

wherein R is hydrogen or hydroxy and M is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl and preferably is hydrogen or a nontoxic, pharmaceutically acceptable salt thereof.

We claim:

1. An acid having the D configuration in the 7-sidechain and the formula

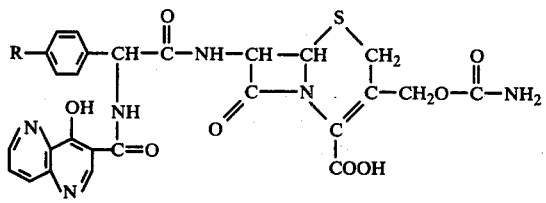

wherein R is hydrogen or hydroxy or a nontoxic, pharmaceutically acceptable salt of said acid or the pivaloyloxymethyl, acetoxymethyl, acetonyl, phenacyl, methoxymethyl, 3-phthalidyl, 5-indanyl, p-nitrobenzyl, $\beta,\beta,\beta$-trichloromethyl or benzhydryl ester of said acid.

2. An acid having the D configuration in the 7-sidechain and the formula

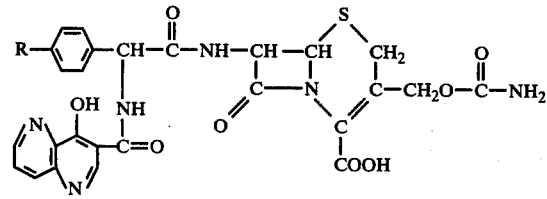

wherein R is hydrogen or hydroxy.

3. The sodium salt of an acid of claim 1.
4. The potassium salt of an acid of claim 1.
5. The nontoxic, pharmaceutically acceptable salt of an acid of claim 1.
6. The pivaloyloxymethyl ester of an acid of claim 1.
7. The acetoxymethyl ester of an acid of claim 1.
8. The acetonyl ester of an acid of claim 1.
9. The phenacyl ester of an acid of claim 1.
10. The methoxymethyl ester of an acid of claim 1.

11. The 3-phthalidyl ester of an acid of claim 1.
12. The 5-indanyl ester of an acid of claim 1.
13. The p-nitrobenzyl ester of an acid of claim 1.
14. β,β,β-trichloroethyl ester of an acid of claim 1.

29. β,β,β-trichloroethyl ester of the acid of claim 16.
30. The benzhydryl ester of the acid of claim 16.
31. The acid having the D configuration in the 7-side-chain and the formula

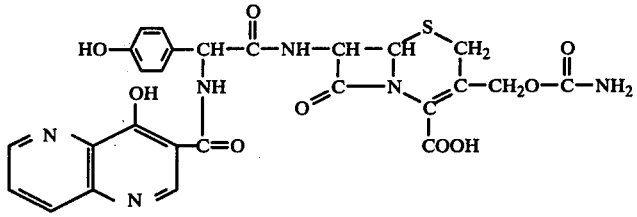

15. The benzhydryl ester of an acid of claim 1.
16. The acid having the D configuration in the 7-side-chain and the formula

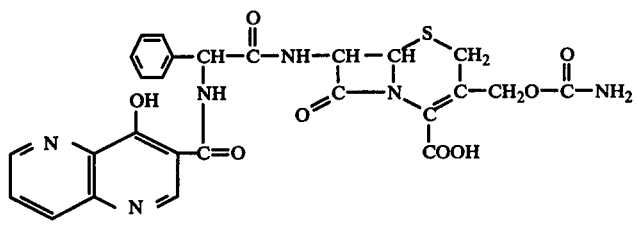

or a nontoxic, pharmaceutically acceptable salt thereof or the pivaloyloxymethyl, acetoxymethyl, acetonyl, phenacyl, methoxymethyl, 3-phthalidyl, 5-indanyl, p-nitrobenzyl, β,β,β-trichloromethyl or benzhydryl ester of said acid.

32. The acid having the D configuration in the 7-side-chain and the formula

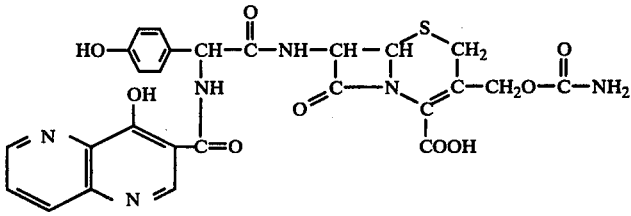

or a nontoxic, pharmaceutically acceptable salt thereof or the pivaloyloxymethyl, acetoxymethyl, acetonyl, phenacyl, methoxymethyl, 3-phthalidyl, 5-indanyl, p-nitrobenzyl, β,β,β-trichloromethyl or benzhydryl ester of said acid.

17. The acid having the D configuration in the 7-side-chain and the formula

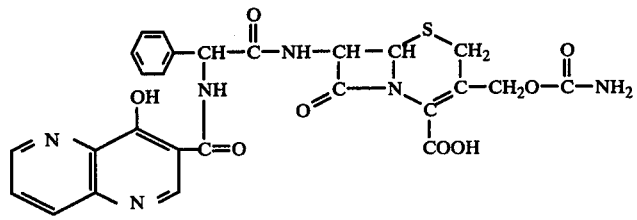

of said acid.

33. The sodium salt of the acid of claim 32.
34. The potassium salt of the acid of claim 32.
35. A nontoxic, pharmaceutically acceptable salt of the acid of claim 31.

18. The sodium salt of the acid of claim 17.
19. The potassium salt of the acid of claim 17.
20. A nontoxic, pharmaceutically acceptable salt of the acid of claim 16.
21. The pivaloyloxymethyl ester of the acid of claim 16.
22. The acetoxymethyl ester of the acid of claim 16.
23. The acetonyl ester of the acid of claim 16.
24. The phenacyl ester of the acid of claim 16.
25. The methoxymethyl ester of the acid of claim 16.
26. The 3-phthalidyl ester of the acid of claim 16.
27. The 5-indanyl ester of the acid of claim 16.
28. The p-nitrobenzyl ester of the acid of claim 16.

36. The pivaloyloxymethyl ester of the acid of claim 31.
37. The acetoxymethyl ester of the acid of claim 31.
38. The acetonyl ester of the acid of claim 31.
39. The phenacyl ester of the acid of claim 31.
40. The methoxymethyl ester of the acid of claim 31.
41. The 3-phthalidyl ester of the acid of claim 31.
42. The 5-indanyl ester of the acid of claim 31.
43. The p-nitrobenzyl ester of the acid of claim 31.
44. β,β,β-trichloroethyl ester of the acid of claim 31.
45. The benzhydryl ester of the acid of claim 31.

* * * * *

Notice of Adverse Decision in Interference

In Interference No. 100,579, involving Patent No. 4,138,554, T. Naito, J. Okumura and M. Oka, 7-[D-α(4-HYDROXY-1,5-NAPHTHYRIDINE-3-CARBOXAMIDO)-α-PHENYL (AND P-HYDROXYPHENYL)ACETAMIDO]-3-CARBAMOYLOXYMETHYL-3-CEPHEM-4-CARBOXYLIC ACIDS, final judgment adverse to the patentees was rendered Dec. 2, 1981, as to claims 1-5, 16-20 and 31-35.

[*Official Gazette April 6, 1982.*]